US012599704B2

(12) United States Patent
Furukawa et al.

(10) Patent No.: US 12,599,704 B2
(45) Date of Patent: Apr. 14, 2026

(54) ENDOSCOPIC FLEXIBLE TUBE, ENDOSCOPIC MEDICAL APPARATUS, AND ENDOSCOPIC-FLEXIBLE-TUBE-BASE-COVERING MATERIAL

(71) Applicant: FUJIFILM Corporation, Tokyo (JP)

(72) Inventors: Kazushi Furukawa, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 519 days.

(21) Appl. No.: 18/147,244

(22) Filed: Dec. 28, 2022

(65) Prior Publication Data

US 2023/0136764 A1 May 4, 2023

Related U.S. Application Data

(63) Continuation of application No. PCT/JP2021/024362, filed on Jun. 28, 2021.

(30) Foreign Application Priority Data

Jun. 29, 2020 (JP) ................................. 2020-111756

(51) Int. Cl.
  *A61L 29/04* (2006.01)
  *A61B 1/005* (2006.01)
(52) U.S. Cl.
  CPC ............ *A61L 29/049* (2013.01); *A61B 1/005* (2013.01)
(58) Field of Classification Search
  None
  See application file for complete search history.

(56) References Cited

U.S. PATENT DOCUMENTS

2001/0029317 A1* 10/2001 Hayakawa .............. A61L 29/08
                                                    600/140
2009/0198021 A1*  8/2009 Ogura ................... A61L 29/049
                                                    525/418
(Continued)

FOREIGN PATENT DOCUMENTS

CN      101502679 A      8/2009
CN      110868906 A      3/2020
(Continued)

OTHER PUBLICATIONS

Extended European Search Report issued Nov. 21, 2023 in Application No. 21832687.4.
Office Action issued Aug. 29, 2023 in corresponding Japanese Patent Application No. 2022-533996.
International Search Report dated Aug. 31, 2021 in International Application No. PCT/JP2021/024362.
Written Opinion dated Aug. 31, 2021 in International Application No. PCT/JP2021/024362.

(Continued)

*Primary Examiner* — Yan Lan
(74) *Attorney, Agent, or Firm* — Sughrue Mion, PLLC

(57) ABSTRACT

An endoscopic flexible tube including a sleeve-shaped flexible-tube base having flexibility, and a cover layer for the flexible-tube base, wherein the cover layer contains (a) at least one of (a1) a polyester resin having a naphthalene structure or (a2) a polyester elastomer having a naphthalene structure, and (b) at least one of (b1) a thermoplastic resin not having a naphthalene structure or (b2) a thermoplastic elastomer not having a naphthalene structure, and, in the cover layer, a ratio of the component (a) to a total amount of the components (a) and (b) is more than 50 mass % and less than 90 mass %; an endoscopic medical apparatus including the endoscopic flexible tube; and a covering material for the endoscopic-flexible-tube base.

6 Claims, 2 Drawing Sheets

(56) References Cited

U.S. PATENT DOCUMENTS

| | | |
|---|---|---|
| 2010/0280319 A1 | 11/2010 | Ogura et al. |
| 2020/0100652 A1 | 4/2020 | Yoshitani et al. |
| 2020/0345327 A1 | 11/2020 | Nakai |
| 2020/0405918 A1 | 12/2020 | Nakai et al. |

FOREIGN PATENT DOCUMENTS

| | | |
|---|---|---|
| JP | 2001-275936 A | 10/2001 |
| JP | 2004-141487 A | 5/2004 |
| JP | 2009-183467 A | 8/2009 |
| JP | 2015-66216 A | 4/2015 |
| WO | 2019/151135 A1 | 8/2019 |
| WO | 2019/189035 A1 | 10/2019 |

OTHER PUBLICATIONS

International Preliminary Report on Patentability including English translation of the Written Opinion dated Dec. 13, 2022 in International Application No. PCT/JP2021/024362.
Japanese Office Action dated Dec. 26, 2023 in corresponding Application No. 2022-533996.
Office Action dated Jul. 11, 2025 in Chinese Application No. 202180043596.1.
Chinese Office Action issued Nov. 21, 2025 in Application No. 202180043596.1.

\* cited by examiner

**ENDOSCOPIC FLEXIBLE TUBE,
ENDOSCOPIC MEDICAL APPARATUS, AND
ENDOSCOPIC-FLEXIBLE-TUBE-BASE-
COVERING MATERIAL**

CROSS-REFERENCE TO RELATED APPLICATIONS

This application is a Continuation of PCT International Application No. PCT/JP2021/024362 filed on Jun. 28, 2021, which claims priority under 35 U.S.C. § 119 (a) to Japanese Patent Application No. 2020-111756 filed in Japan on Jun. 29, 2020. Each of the above applications is hereby expressly incorporated by reference, in its entirety, into the present application.

BACKGROUND OF THE INVENTION

1. Field of the Invention

The present invention relates to an endoscopic flexible tube, an endoscopic medical apparatus, and an endoscopic-flexible-tube-base-covering material.

2. Description of the Related Art

The endoscope is a medical apparatus for observing, for example, the body cavity, the alimentary canal, or the esophagus of the patient. Since it is inserted into the body and used, it desirably does not damage internal organs and does not cause pain, uncomfortableness, or the like to the patient. In order to meet such needs, as the flexible tube constituting the insertion section of an endoscope, a spiral tube formed by spirally winding a flexible and bendable metal strip is employed. Furthermore, it is designed such that its periphery is covered with a flexible polymer material so as not to cause irritation, damage, or the like to linings of the esophagus, the alimentary canal, and the body cavity, for example.

The endoscope for observing the interior of the human body is repeatedly used. For this reason, in the endoscope, the flexible tube constituting the insertion section needs to be, after each use, washed and disinfected using a chemical. In particular, in the cases of insertion into highly susceptible regions such as bronchi, cleanliness of the sterilization grade, which is above the disinfection grade, is required. Thus, endoscopic flexible tubes have come to be required to have high resistance for resisting even repeated sterilization treatments.

For example, JP2004-141487A states that, in an endoscopic flexible tube in which the surface of a flexible-tube material is covered with an outer cover, the outer cover is constituted by a polyester elastomer using, as a hard segment, polybutylene naphthalate, so that the outer cover has improved heat resistance and improved hydrolysis resistance and can be subjected to autoclaving (high-pressure water-vapor sterilization).

In addition, JP2009-183467A states that, for an endoscopic flexible tube covered with an outer cover formed of an endoscopic elastomer shaped body provided by cross-linking two or more thermoplastic polyester elastomers, the outer cover is less likely to undergo deterioration due to various chemicals.

SUMMARY OF THE INVENTION

As a sterilization treatment for endoscopic flexible tubes, the above-described autoclave treatment is performed. Alternatively, in recent years, from the viewpoint of suppression of moisture-heat deterioration of endoscopic flexible tubes, chemical sterilization treatments using hydrogen peroxide plasma, ethylene oxide gas, or the like have come to be widely performed. In addition, recently, a sterilization treatment using ozonated water prepared by dissolving a very small amount of ozone ($O_3$) in water has also come to be performed. This ozonated water generates a strong active species such as a hydroxy radical and its oxidizing power is stronger than that of hydrogen peroxide gas. Thus, as organic materials that resist the sterilization treatment using ozonated water, just fluororesins are known.

Even in the case of not being subjected to autoclave sterilization treatments, endoscopic flexible tubes need to have moisture-heat resistance. Specifically, for such an endoscope, the flexible-tube section is inserted into the body and used under irradiation with strong light to observe the target part within the body or to treat the lesion. Such observation, treatment, and the like under strong light are performed while the observation window (lens) and the like of the flexible tube are washed with water. In other words, the endoscope being inserted into the body is exposed to heat radiated from the light source and moisture and is placed in the moisture-heat environment. Thus, while such observation within the body or lesion treatments are repeated, the cover layer (outer cover) of the flexible tube deteriorates and water vapor tends to enter the inside of the flexible tube, which also results in acceleration of deterioration of various members constituting the endoscope. Recently, with an increasing demand for reduction in the diameter of endoscopic flexible tubes, the thickness of the cover layers has come to be reduced and there has been a demand for higher moisture-heat resistance (water-vapor barrier performance) of the cover layers.

Under such circumstances, objects of the present invention are to provide an endoscopic flexible tube that exhibits high gas barrier performance even after being exposed to a moisture-heat environment for a long period of time, and that exhibits high sterilization resistance against a strong sterilization treatment using ozonated water, and an endoscopic medical apparatus using the endoscopic flexible tube. Another object of the present invention is to provide an endoscopic-flexible-tube-base-covering material suitable for forming the cover layer of the endoscopic flexible tube.

The inventors of the present invention performed thorough studies on how to achieve the above-described objects and, as a result, have found the following: a polymer blend material including, in a specific ratio, a polyester resin or polyester elastomer having a naphthalene structure and a thermoplastic resin or thermoplastic elastomer not having a naphthalene structure is used as a constituent material of a cover layer constituting an endoscopic flexible tube, so that, in the cover layer formed, the polymers are phase-separated from each other, but form a composition homogeneous as a whole; even when this cover layer formed as a thin layer is exposed to a moisture-heat environment for a long period of time, it exhibits high gas barrier performance and has such resistance that is less likely to deteriorate even after being subjected to a strong sterilization treatment using ozonated water. On the basis of such findings, further studies have been performed to accomplish the present invention.

The above-described objects have been achieved by the following means.

<1>

An endoscopic flexible tube including a sleeve-shaped flexible-tube base having flexibility, and a cover layer for the flexible-tube base, wherein the cover layer contains components (a) and (b) below and, in the cover layer, a ratio of the component (a) to a total amount of the components (a) and (b) is more than 50 mass % and less than 90 mass %:

(a) at least one of (a1) a polyester resin having a naphthalene structure or (a2) a polyester elastomer having a naphthalene structure; and (b) at least one of (b1) a thermoplastic resin not having a naphthalene structure or (b2) a thermoplastic elastomer not having a naphthalene structure.

<2>

The endoscopic flexible tube according to <1>, wherein the (b1) thermoplastic resin not having a naphthalene structure includes at least one of a polyolefin resin, a polydiene resin, a polystyrene resin, a polyacrylic resin, a polyvinyl resin, a polyester resin, a polyamide resin, a polycarbonate resin, a polyurethane resin, a polysulfone resin, a polyether resin, or a fluorine-containing resin.

<3>

The endoscopic flexible tube according to <2>, wherein the (b1) thermoplastic resin not having a naphthalene structure includes at least one of a polyolefin resin, a polydiene resin, or a polystyrene resin.

<4>

The endoscopic flexible tube according to any one of <1> to <3>, wherein the (b2) thermoplastic elastomer not having a naphthalene structure includes at least one of a polystyrene elastomer, a polyolefin elastomer, a polyvinyl chloride elastomer, a polyurethane elastomer, a polyester elastomer, or a polyamide elastomer.

<5>

The endoscopic flexible tube according to <4>, wherein the (b2) thermoplastic elastomer not having a naphthalene structure includes at least one of a polystyrene elastomer or a polyolefin elastomer.

<6>

The endoscopic flexible tube according to any one of <1> to <5>, wherein, in the cover layer, the component (a) and the component (b) are phase-separated from each other.

<7>

The endoscopic flexible tube according to any one of <1> to <6>, wherein the cover layer contains a compatibilizer.

<8>

An endoscopic medical apparatus including the endoscopic flexible tube according to any one of <1> to <7>.

<9>

An endoscopic-flexible-tube-base-covering material including components (a) and (b) below, wherein a ratio of the component (a) to a total amount of the components (a) and (b) is more than 50 mass % and less than 90 mass %:

(a) at least one of (a1) a polyester resin having a naphthalene structure or (a2) a polyester elastomer having a naphthalene structure; and (b) at least one of (b1) a thermoplastic resin not having a naphthalene structure or (b2) a thermoplastic elastomer not having a naphthalene structure.

An endoscopic flexible tube according to the present invention exhibits high gas barrier performance even after being exposed to a moisture-heat environment for a long period of time and exhibits high sterilization resistance against a strong sterilization treatment using ozonated water. An endoscopic medical apparatus according to the present invention is an apparatus that includes the above-described endoscopic flexible tube having good properties. A covering material according to the present invention is suitable as a polymer material constituting a cover layer of an endoscopic flexible tube according to the present invention.

DESCRIPTION OF THE PREFERRED EMBODIMENTS

Figure 1:
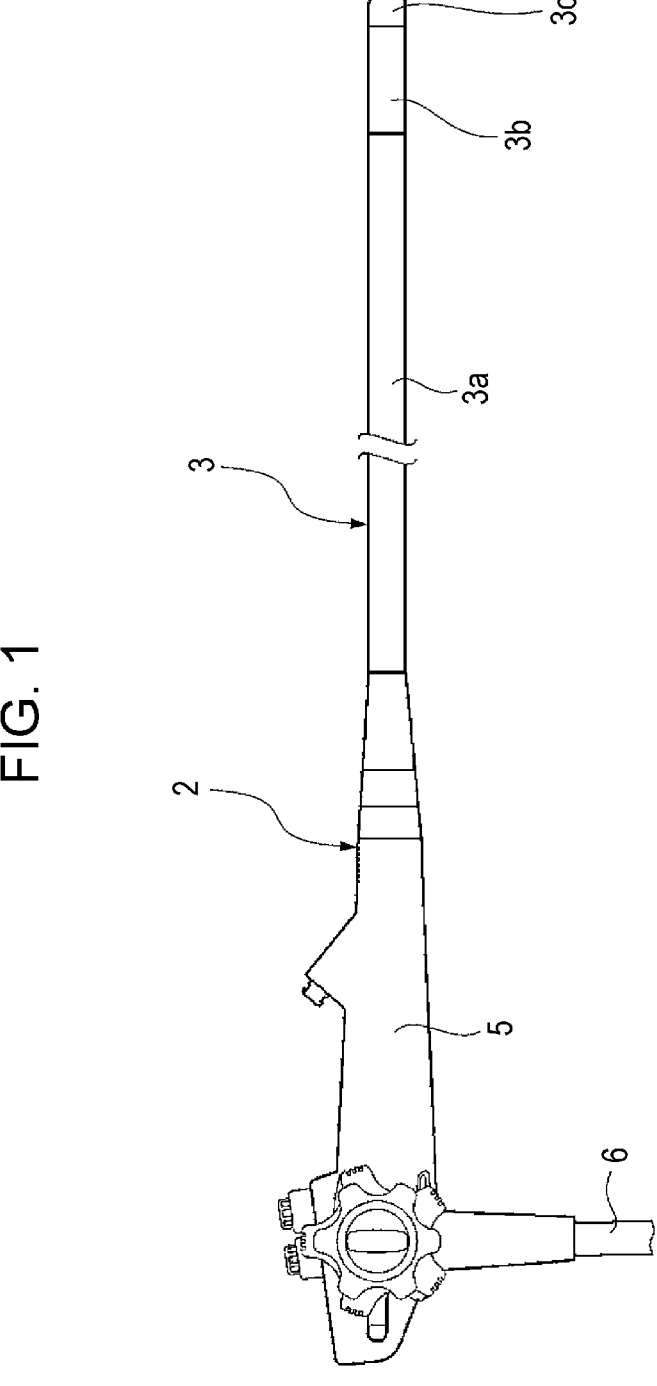
FIG. 1 is an external view illustrating the configuration of an electronic endoscope.

A preferred embodiment of an endoscopic medical apparatus according to the present invention will be described with reference to an electronic endoscope serving as an example. The electronic endoscope in which an endoscopic flexible tube is incorporated (hereafter, the endoscopic flexible tube may also be simply referred to as "flexible tube") is widely used as a medical apparatus. In the example illustrated in FIG. 1, an electronic endoscope 2 includes an insertion section 3 to be inserted into the body, a main-body operation section 5 coupled to the base-end portion of the insertion section 3, and a universal cord 6 connected to a processor device and a light source device. The insertion section 3 is constituted by a flexible tube 3a coupled to the main-body operation section 5, an angle portion 3b coupled to the flexible tube 3a, and a distal-end portion 3c coupled to the distal end of the angle portion 3b and including therein an image pick-up device (not shown) for imaging the inside of the body. The flexible tube 3a, which accounts for most of the length of the insertion section 3, has flexibility substantially over the whole length; in particular, the portion inserted into the body has a more flexible structure.

Flexible Tube

Figure 2:
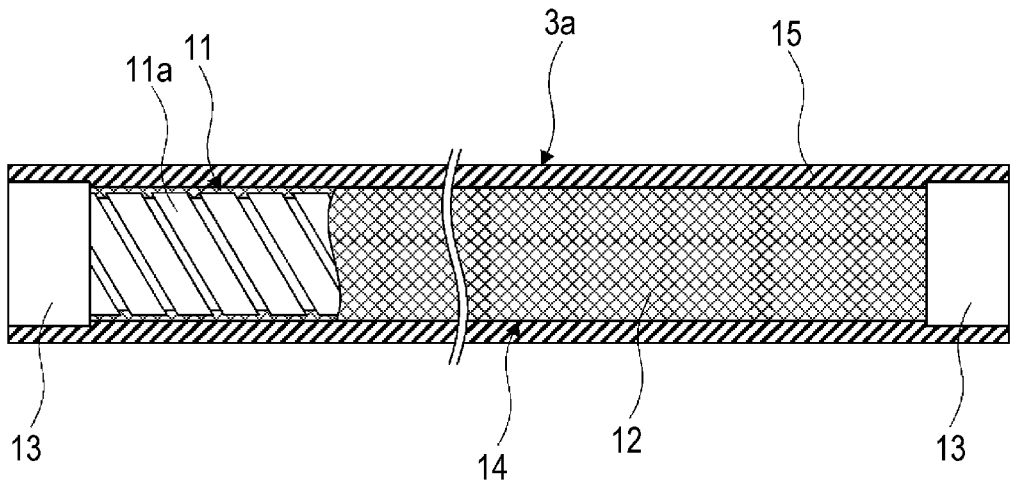
FIG. 2 is a partial sectional view illustrating the schematic configuration of an endoscopic flexible tube.

The flexible tube 3a (endoscopic flexible tube) has, as illustrated in FIG. 2, a configuration having a flexible-tube base 14 in which a spiral tube 11, which is disposed on the innermost side and formed by spirally winding a metal strip 11a, is covered with a sleeve-shaped mesh body 12 formed by knitting metal wires, and both ends are fitted with metal caps 13, the flexible-tube base 14 having an outer periphery surface covered with a cover layer 15. The spiral tube 11 is drawn as a single layer alone, but may alternatively have a configuration of a coaxial double layer. Note that the cover layer 15 is, in order to clearly illustrate the layer structure, drawn thickly relative to the diameter of the flexible-tube base 14.

In this embodiment, the cover layer 15 is formed so as to have a thickness that is substantially uniform in the longitudinal direction (axial direction) of the flexible-tube base 14. The cover layer 15 has a thickness of, for example, 0.1 to 0.6 mm; the flexible tube 3a has an outer diameter D of, for example, 2.0 to 10.0 mm, preferably 3.0 to 8.0 mm. The flexible-tube base 14 has an outer diameter of, for example, 1.6 to 9.6 mm, preferably 2.2 to 7.8 mm. When the insertion section 3 is inserted into the bronchus, the cover layer 15 preferably has a thickness of 0.1 to 0.3 mm, the flexible tube 3a preferably has an outer diameter D of 3.0 to 5.0 mm, and the flexible-tube base 14 preferably has an outer diameter of 2.4 to 4.8 mm.

An endoscopic flexible tube according to the present invention includes a sleeve-shaped flexible-tube base having flexibility, and a cover layer covering the flexible-tube base, wherein the cover layer contains components (a) and (b) below:

(a) at least one of (a1) a polyester resin having a naphthalene structure or (a2) a polyester elastomer having a naphthalene structure; and

5

(b) at least one of (b1) a thermoplastic resin not having a naphthalene structure or (b2) a thermoplastic elastomer not having a naphthalene structure.

In the present invention, the ratio of the component (a) to the total amount of the components (a) and (b) in the cover layer is more than 50 mass % and less than 90 mass %.

In an endoscopic flexible tube according to the present invention, the component (a) constituting the cover layer has a naphthalene structure, so that the component (a) undergoes intramolecularly and intermolecularly strong interaction. Thus, when the component (a) and the component (b) are blended homogeneously in a predetermined ratio, the two components do not easily form a homogeneous mixture, but form a micrometer-level phase-separation state. For example, a phase-separation state is formed such that the component (a) has a continuous phase and the component (b) has a disperse phase. When such a phase-separation state is formed, the phases repel each other, so that, in each phase, the polymer segments form a strong aggregation state inferentially. This inferentially results in improvement in the water-vapor barrier performance and also effective improvement in the ozonated-water resistance. To the improvement in the barrier performance, the large molecular area specific to the naphthalene also effectively contributes inferentially. Note that the continuous phase and the disperse phase are not necessarily distinguished from each other clearly; of the component (a) and the component (b), the component (a), which has a larger mixing amount, tends to provide more regions continuously (successively) present in the whole cover layer. Such disperse phases (phases present in the form of particles) individually have a particle size of, in plan view, preferably about 1 to about 50 also preferably about 1 to about 30 μm.

The cover layer 15 may be a single layer or may be plural layers constituted by layers different from each other in composition (plural layers different from each other in compositional ratio of the constituent dicarboxylic acid component or diol component). The cover layer 15 is preferably a single layer. When the cover layer 15 is plural layers, at least one layer is constituted by an endoscopic-flexible-tube-base-covering material according to the present invention, and the outermost layer is preferably constituted by an endoscopic-flexible-tube-base-covering material according to the present invention. A flexible tube according to the present invention may have, on the outside of the cover layer, a topcoat layer. For the configuration of the topcoat layer, reference can be made to descriptions of, for example, JP2015-16261A.

Polyester Having Naphthalene Structure [Component (a)]

The component (a) is at least one of (a1) a polyester resin having a naphthalene structure or (a2) a polyester elastomer having a naphthalene structure.

The polyester resin of the component (a1) and the polyester elastomer of the component (a2) are preferably constituted by a dicarboxylic acid component including a naphthalenedicarboxylic acid component and a diol component.

In the present invention, a specific example of the dicarboxylic acid component preferred as the naphthalenedicarboxylic acid component is a 2,6-naphthalenedicarboxylic acid component.

First, the component (a1) being a polyester resin having a naphthalene structure will be described.

The component (a1) being a polyester resin having a naphthalene structure preferably has a naphthalenedicarboxylic acid component. The polyester resin having a naphthalenedicarboxylic acid component may have, as a dicarboxylic acid component, a dicarboxylic acid component other than the naphthalenedicarboxylic acid component.

The dicarboxylic acid component other than the naphthalenedicarboxylic acid component is not particularly limited and those ordinarily used as dicarboxylic acid components constituting polyester resins are widely applicable. Examples include terephthalic acid, isophthalic acid, phthalic acid, sodium 5-sulfoisophthalate, oxalic acid, succinic acid, adipic acid, sebacic acid, azelaic acid, dodecanedioic acid, dimer acid, maleic anhydride, maleic acid, fumaric acid, itaconic acid, citraconic acid, mesaconic acid, and cyclohexanedicarboxylic acid. Such dicarboxylic acid components may be used alone or in combination of two or more thereof.

As the component (a1) being a polyester resin having a naphthalene structure, those ordinarily used as diol components constituting polyester resins are widely applicable. Examples include constituent components derived from ethylene glycol, diethylene glycol, 1,3-propanediol, 1,4-butanediol, neopentyl glycol, 1,6-hexanediol, cyclohexanedimethanol, triethylene glycol, bisphenol A, or bisphenol S, for example. Such diol components are used alone or in combination of two or more thereof.

The component (a1) being a polyester resin having a naphthalene structure may have a hydroxycarboxylic acid component as a constituent component. Examples of the hydroxycarboxylic acid component include constituent components derived from ε-caprolactone, lactic acid, or 4-hydroxybenzoic acid, for example. These hydroxycarboxylic acid components may be used alone or in combination of two or more thereof.

The component (a1) being a polyester resin having a naphthalene structure may be a homopolymer or copolymer constituted by such a component and may further contain a small amount of a trifunctional compound component such as trimellitic acid, trimesic acid, pyromellitic acid, trimethylolpropane, glycerol, or pentaerythritol.

As such components (a1) being a polyester resin having a naphthalene structure, two or more homopolymers or copolymers constituted by the above-described components may be used in combination.

Next, the component (a2) being a polyester elastomer having a naphthalene structure will be described.

The component (a2) being a polyester elastomer having a naphthalene structure preferably has a naphthalenedicarboxylic acid component. More preferred is a copolymer constituted by a hard segment formed of a crystalline polyester chain including a dicarboxylic acid component including a naphthalenedicarboxylic acid component and a low-molecular-weight diol component as constituent components, and at least any one soft segment of the following (i) to (iii):

(i) a soft segment constituted by an aliphatic polyester chain, (ii) a soft segment constituted by an aliphatic polymer diol component, and (iii) a soft segment constituted by a polyester chain constituted by an aliphatic polymer diol component and a dicarboxylic acid component including an aromatic dicarboxylic acid.

In other words, the naphthalene structure may be introduced into any one of or both of the hard segment and the soft segment, and is preferably at least introduced into the hard segment.

Hereinafter, a polyester elastomer in which the hard segment has a naphthalene structure will be described.

For the polyester elastomer in which the hard segment has a naphthalene structure, the hard segment preferably has a naphthalenedicarboxylic acid component. When the hard segment has a naphthalenedicarboxylic acid component, the dicarboxylic acid component of the hard segment may be entirely a naphthalenedicarboxylic acid component, or the hard segment may have a dicarboxylic acid component other than naphthalenedicarboxylic acid components. As the dicarboxylic acid component other than naphthalenedicarboxylic acid components that constitutes the hard segment, those ordinarily used as dicarboxylic acid components constituting hard segments of ordinary polyester elastomers are widely applicable. Examples include the dicarboxylic acid components other than naphthalenedicarboxylic acid components having been described in the description of the component (a1) being a polyester resin having a naphthalene structure; it can have one or two or more of such dicarboxylic acid components. In particular, the dicarboxylic acid component other than naphthalenedicarboxylic acid components that constitutes the hard segment preferably includes an aromatic dicarboxylic acid component (dicarboxylic acid component having an aromatic ring); preferably 50 mass % or more (preferably 70 mass % or more, more preferably 80 mass % or more, still more preferably 90 mass % or more) of the dicarboxylic acid component other than naphthalenedicarboxylic acid component is an aromatic dicarboxylic acid component. The dicarboxylic acid component other than naphthalenedicarboxylic acid components that constitutes the hard segment is also preferably entirely an aromatic dicarboxylic acid component.

As the diol component constituting the hard segment, those ordinarily used as diol components constituting polyester resins are widely applicable. Examples include the diol components having been described in the component (a1) being a polyester resin having a naphthalene structure; it can have one or two or more of the diol components.

The hard segment may have one or two or more of the hydroxycarboxylic acid components having been described in the description of the component (a1) being a polyester resin having a naphthalene structure, as constituent components.

The hard segment may be a homopolymer or copolymer constituted by the above-described constituent components.

When the soft segment is the (i) aliphatic polyester chain, the dicarboxylic acid component constituting the aliphatic polyester chain is not particularly limited as long as it is an aliphatic dicarboxylic acid component. For example, it can have a constituent component derived from oxalic acid, succinic acid, adipic acid, sebacic acid, azelaic acid, dodecanedioic acid, dimer acid, maleic acid, fumaric acid, itaconic acid, citraconic acid, mesaconic acid, or cyclohexanedicarboxylic acid, for example. The aliphatic polyester chain can have one or two or more of these dicarboxylic acid components.

The diol component of the aliphatic polyester chain constituting the soft segment is not particularly limited as long as it is an aliphatic diol component. Examples include aliphatic diol components derived from ethylene glycol, diethylene glycol, triethylene glycol, propylene glycol, dipropylene glycol, 3-methyl-1,5-pentanediol, 1,3-propanediol, 1,4-butanediol, 1,9-nonanediol, neopentyl glycol, 1,5-pentanediol, 1,6-hexanediol, decamethylene glycol, or cyclohexanedimethanol, for example. It can have one or two or more of these diol components. The aliphatic polyester chain also preferably has, as a diol component, an aliphatic polymer diol component. Examples of the aliphatic polymer diol component include polyalkylene glycols such as polyethylene glycol, polypropylene glycol, and polytetramethylene ether glycol; it can have one or two or more of these aliphatic polymer diol components. In the present invention, the polyalkylene glycol is a compound represented by $HO—[(CH_2)_mO]_n—H$. Here, m is preferably 1 to 12, more preferably 2 to 10, still more preferably 2 to 8, particularly preferably 2 to 6. n is preferably 5 to 100, more preferably 10 to 50.

Alternatively, when the soft segment is the (ii) amorphous soft segment derived from an aliphatic polymer diol, this aliphatic polymer diol is not particularly limited as long as it is an aliphatic polymer diol. Examples include polyalkylene glycols such as polyethylene glycol, polypropylene glycol, and polytetramethylene ether glycol. The polyester elastomer can have a structure having, as the soft segment, an aliphatic polymer diol component derived from one or two or more of these. The structure of the polyalkylene glycol has been described above.

Alternatively, when the soft segment is the (iii) soft segment constituted by a polyester chain constituted by an aliphatic polymer diol component and a dicarboxylic acid component including an aromatic dicarboxylic acid, this aliphatic polymer diol component is not particularly limited and may be, for example, the constituent component derived from an aliphatic polymer diol having been described in (ii) above. The aromatic dicarboxylic acid component may be a constituent component derived from naphthalene dicarboxylic acid. In the case of including a dicarboxylic acid component other than aromatic dicarboxylic acid components, this dicarboxylic acid component may be the dicarboxylic acid component having been described in (i) above.

Examples of the component (a) having a naphthalene structure and being commercially available include TQB-KET30 (manufactured by Teijin Chemicals Ltd.) and PEL-PRENE EN type (manufactured by TOYOBO CO., LTD.).

Such polyesters having a naphthalene structure may be used alone or may be used in combination of two or more thereof.

Thermoplastic Resin and Thermoplastic Elastomer not Having Naphthalene Structure [Component (b)]

The component (b) is at least one of (b1) a thermoplastic resin not having a naphthalene structure or (b2) a thermoplastic elastomer not having a naphthalene structure. The component (b) is not particularly limited as long as it is a thermoplastic resin or thermoplastic elastomer not having a naphthalene structure; in particular, preferred are those having a small number of polar functional groups and having high hydrophobicity. When the component (b) has higher hydrophobicity, it provides stronger interaction with the naphthalene structure of the component (a), to further improve, between the phases, the barrier function of the cover layer, to improve the action of suppressing permeability of water-vapor gas under moisture-heat conditions and permeation of active species generated from ozonated water, such as a hydroxy radical inferentially.

The thermoplastic resin of the component (b1) preferably includes at least one of a polyolefin resin, a polydiene resin, a polystyrene resin, a polyacrylic resin, a polyvinyl resin, a polyester resin, a polyamide resin, a polycarbonate resin, a polyurethane resin, a polysulfone resin, a polyether resin, or a fluorine-containing resin.

The thermoplastic resin of the component (b1) more preferably includes at least one of a polyolefin resin, a polydiene resin, or a polystyrene resin.

Polyolefin Resin

In the present invention, in the case of referring to a polyolefin resin, it means a resin constituted by a polymer including, as a constituent component, an olefin component. The polymer including an olefin component may be an olefin homopolymer or may be an olefin copolymer. The olefin copolymer may be a copolymer of an olefin and another olefin or a copolymer of an olefin and a non-olefin compound having a carbon-carbon double bond, such as a vinyl compound.

The olefin component is a constituent unit derived from an alkene. Examples of the olefin compound (alkene) from which the olefin component of the polyolefin resin is derived include ethylene, propylene, 1-butene, and 4-methyl-1-pentene.

Examples of the polyolefin resin include low-density polyethylene resins, ultra-low-density polyethylene resins, high-density polyethylene resins, linear low-density polyethylene resins, polypropylene resins, polymethylpentene resins, and resins constituted by ethylene-vinyl acetate copolymers or the like.

When the component (b1) includes a polyolefin resin, one or two or more polyolefin resins may be used.

Examples of such polyolefin resins that are commercially available include NOVATEC PP (manufactured by Japan Polypropylene Corporation), NOVATEC LD (manufactured by Mitsubishi Chemical Corporation), NOVATEC LL (manufactured by Mitsubishi Chemical Corporation), and NOVATEC HD (manufactured by Mitsubishi Chemical Corporation).

Polydiene Resin

In the present invention, in the case of referring to a polydiene resin, it is a resin constituted by a polymer including, as a constituent component, a diene component. Note that, in the present invention, when this polymer includes an olefin component, even in spite of including a diene component, it is classified as a polyolefin resin. The diene component is a constituent unit derived from a diene compound. Examples of the diene compound from which the diene component of the polydiene resin is derived include 1,3-butadiene and 2-methyl-1,3-butadiene (isoprene).

Examples of the polydiene resin include resins constituted by polybutadiene, a styrene-butadiene copolymer, polyisoprene, an acrylonitrile-butadiene-styrene copolymer, or the like.

When the component (b1) includes a polydiene resin, one or two or more of such polydiene resins may be used.

Examples of such polydiene resins that are commercially available include JSR1500 (manufactured by JSR Corporation).

Polystyrene Resin

The polystyrene resin is a resin constituted by a polymer including, as a constituent component, a styrene component. Note that, in the present invention, when this polymer includes an olefin component, it is classified as a polyolefin resin. Alternatively, when this polymer does not have an olefin component, but has a diene component, it is classified as a polydiene resin.

Examples of the polystyrene resin include resins constituted by polystyrene, an acrylonitrile-styrene copolymer, or the like.

Examples of such polystyrene resins that are commercially available include CEVIAN N (manufactured by Daicel Corporation).

Polyacrylic Resin

In the present invention, in the case of referring to a polyacrylic resin, it is a resin constituted by a polymer having, as a constituent component, at least one of a component having a (meth)acryloyl group or a (meth)acrylonitrile component. Note that, in the present invention, when this polymer includes an olefin component, it is classified as a polyolefin resin. Alternatively, when this polymer does not have an olefin component, but has a diene component, it is classified as a polydiene resin. Alternatively, when this polymer does not have an olefin component or a diene component, but has a styrene component, it is classified as a polystyrene resin. The "(meth)acryloyl group" means an acryloyl group and/or a methacryloyl group. The same applies to "(meth)acrylonitrile".

The constituent component having a (meth)acryloyl group is at least one of a (meth)acrylic acid component or a (meth)acrylic acid ester component. Examples of the (meth)acrylic acid ester include methyl methacrylate, methyl acrylate, ethyl acrylate, ethyl methacrylate, butyl methacrylate, butyl acrylate, methoxyethyl acrylate, and ethoxyethyl acrylate.

The polyacrylic resin is, for example, a resin constituted by polymethyl methacrylate, polyacrylonitrile, or the like.

Examples of such polyacrylic resins that are commercially available include ACRYPET VH (manufactured by Mitsubishi Chemical Corporation).

Polyvinyl Resin

In the present invention, in the case of referring to a polyvinyl resin, it is, of resins constituted by polymers having constituent components derived from vinyl compounds, a resin that is not classified as the polyolefin resin, the polydiene resin, the polyacrylic resin, or the polystyrene resin.

Examples of the polyvinyl resin include polyvinyl chloride resins, polyvinylidene chloride resins, polyvinyl acetate resins, and polyvinyl alcohol resins.

Examples of such polyvinyl resins that are used in the present invention and that are commercially available include KANEVINYL (manufactured by KANEKA CORPORATION).

Polyester Resin

The polyester resin not having a naphthalene structure is a polyester resin that does not have a naphthalene structure in a dicarboxylic acid component, a diol component, or a hydroxycarboxylic acid component. As the dicarboxylic acid component, the diol component, or the hydroxycarboxylic acid component that can constitute the polyester resin not having a naphthalene structure, of the components having been described in the (a1) polyester resin, components not having a naphthalene structure are appropriately applicable.

Examples of this polyester resin include polyethylene terephthalate and polybutylene terephthalate.

Examples of such polyester resins that do not have a naphthalene structure, that are used in the present invention, and that are commercially available include NOVADURAN 5010CR2 (manufactured by Mitsubishi Chemical Corporation).

Polyamide Resin

The polyamide resin may be a crystalline polyamide or an amorphous polyamide. In the present invention, in the case of referring to a polyamide resin, it is intended to include a polyamide-imide resin.

Examples of the crystalline polyamide include aliphatic polyamides and aromatic polyamides.

Examples of the aliphatic polyamides include poly ε-caproamide (polyamide 6), polynonaneamide (polyamide 9), polytetramethyleneadipamide (polyamide 46), polyhexamethyleneadipamide (polyamide 66), a polycaproamide/polyhexamethyleneadipamide copolymer (polyamide 6/66), polyundecamide (polyamide 11), a polycaproamide/polyundecamide copolymer (polyamide 6/11), polydodecamide (polyamide 12), a polycaproamide/polydodecamide copolymer (polyamide 6/12), polyhexamethylenesebacamide (polyamide 610), polydecamethylenesebacamide (polyamide 1010), polyhexamethylenedodecamide (polyamide 612), polydecamethylenedodecamide (polyamide 1012), polyundecamethyleneadipamide (polyamide 116), and mixtures and copolymers of the foregoing.

Examples of the aromatic polyamides include polyhexamethyleneisophthalamide (polyamide 6I), polyhexamethyleneterephthalamide (polyamide 6T), a polyhexamethyleneterephthalamide/polyhexamethyleneisophthalamide copolymer (polyamide 6T/6I), a polycaproamide/polyhexamethyleneterephthalamide copolymer (polyamide 6/6T), a polycaproamide/polyhexamethyleneisophthalamide copolymer (polyamide 6/6I), a polyhexamethyleneadipamide/polyhexamethyleneterephthalamide copolymer (polyamide 66/6T), a polyhexamethyleneadipamide/polyhexamethyleneisophthalamide copolymer (polyamide 66/6I), polytrimethylhexamethyleneterephthalamide (polyamide TMDT), polybis(4-aminocyclohexyl)methanedodecamide (polyamide PACM12), polybis(3-methyl-4-aminocyclohexyl) methanedodecamide (nylon dimethyl PACM12), poly-m-xylyleneadipamide (polyamide MXD6), polydecamethyleneterephthalamide (polyamide 10T), polyundecamethyleneterephthalamide (polyamide 11T), and mixtures and copolymers of the foregoing.

Examples of the amorphous polyamides include a polycondensation product of isophthalic acid/terephthalic acid/1,6-hexanediamine/bis(3-methyl aminocyclohexyl)methane, a polycondensation product of terephthalic acid/2,2,4-trimethyl-1,6-hexanediamine/2,4,4-trimethyl-1,6-hexanediamine, a polycondensation product of isophthalic acid/bis(3-methyl-4-aminocyclohexyl)methane/w-laurolactam, a polycondensation product of isophthalic acid/terephthalic acid/1,6-hexanediamine, a polycondensation product of isophthalic acid/2,2,4-trimethyl-1,6-hexanediamine/2,4,4-trimethyl-1,6-hexanediamine, a polycondensation product of isophthalic acid/terephthalic acid/2,2,4-trimethyl-1,6-hexanediamine/2,4,4-trimethyl-1,6-hexanediamine, and a polycondensation product of isophthalic acid/terephthalic acid/another diamine component.

One or two or more of such polyamide resins are used.

Polycarbonate Resin

The polycarbonate resin is a resin constituted by a polymer in which constituent components are linked together via —O—C(=O)—O— bonds (polymer having, in the main chain, a plurality of —O—C(=O)—O— bonds).

Examples of such polycarbonate resins that are used in the present invention and that are commercially available include IUPILON S-2000 (manufactured by Mitsubishi Chemical Corporation).

Polyurethane Resin

The polyurethane resin used in the present invention is a resin constituted by a polymer in which constituent components are linked together via urethane bonds (polymer having, in the main chain, a plurality of urethane bonds).

Examples of such polyurethane resins that are used in the present invention and that are commercially available include VULKOLLAN (manufactured by Bayer AG).

Polysulfone Resin

The polysulfone resin is a resin constituted by a polymer in which constituent components are linked together via sulfonyl groups (—S(=O)$_2$—) (polymer having, in the main chain, a plurality of —S(=O)$_2$— bonds).

Examples of such polysulfone resins that are used in the present invention and that are commercially available include Udel P1700 (manufactured by Solvay).

Polyether Resin

The polyether resin is a resin constituted by a polymer in which constituent components are linked together via ether bonds (polymer having, in the main chain, a plurality of ether bonds). Note that, in the present invention, even in the case where this polymer has, in the polymer chain, ether bonds, when it also corresponds to any one of the resins having been described above as the component (b1), it is classified as such a corresponding resin.

Examples of the polyether resin include polyphenylene ether resins, polyether imide resins, polyether ketone resins, and polyether ether ketone resins.

Fluorine-Containing Resin

The fluorine-containing resin is a polymer having a fluorine atom as a substituent. In the present invention, when this polymer has a fluorine atom, even in the case where it corresponds to any one of the resins having been described above as the component (b1), it is classified as a fluorine-containing resin.

Examples of the fluorine-containing resin include polytetrafluoroethylene resins, tetrafluoroethylene-perfluoroalkoxyethylene copolymers, and polyvinylidene fluoride resins.

Examples of such fluorine-containing resins that are commercially available include NEOFLON PFA (manufactured by DAIKIN INDUSTRIES, LTD.).

The thermoplastic elastomer of the component (b2) preferably includes at least one of a polystyrene elastomer, a polyolefin elastomer, a polyvinyl chloride elastomer, a polyurethane elastomer, a polyester elastomer, or a polyamide elastomer.

The thermoplastic elastomer of the component (b2) more preferably includes at least one of a polystyrene elastomer or a polyolefin elastomer.

Polystyrene Elastomer

The polystyrene elastomer is an elastomer having, as the hard segment, a polystyrene structure. It may have, as the soft segment, for example, a polybutadiene structure, a polyisoprene structure, or a hydrogenated polybutadiene structure.

Examples of such polystyrene elastomers that are commercially available include Tefabloc 4300C (manufactured by Mitsubishi Chemical Corporation).

Polyolefin Elastomer

The polyolefin elastomer is an elastomer having, as the hard segment, a crystalline polyethylene structure or a crystalline polypropylene structure. Examples of the soft segment include an ethylene-propylene-diene rubber (EPDM) structure, a polyisobutylene rubber (IIR) structure, an ethylene-vinyl acetate copolymer structure, an ethylene-ethyl acrylate copolymer structure, a chlorinated polyethylene structure, and an amorphous polyethylene structure.

Examples of such polyolefin elastomers that are commercially available include EXCELINK 1700B (manufactured by JSR Corporation).

Polyvinyl Chloride Elastomer

The polyvinyl chloride elastomer is an elastomer having, as the hard segment, a crystalline polyvinyl chloride structure. Examples of the soft segment include an acrylonitrile-butadiene rubber structure, and a plasticized polyvinyl chloride structure.

Examples of such polyvinyl chloride elastomers that are commercially available include SUNPRENE F1469 (manufactured by Mitsubishi Chemical Corporation).

Polyurethane Elastomer

The polyurethane elastomer may be, for example, an elastomer including structure units that are a hard segment formed of a diol component and a diisocyanate component and a soft segment formed of polyether or aliphatic polyester.

Examples of such polyurethane elastomers that are commercially available include MIRACTRAN (manufactured by Nippon Miractran Company Limited).

Polyester Elastomer

The polyester elastomer not having a naphthalene structure is a polyester elastomer not having a naphthalene structure in a dicarboxylic acid component, a diol component, or a hydroxycarboxylic acid component. As the dicarboxylic acid component, the diol component, and the hydroxycarboxylic acid component that can constitute the polyester elastomer not having a naphthalene structure, of the components having been described above in the (a1) polyester elastomer, those not having a naphthalene structure are appropriately applicable.

Examples of such polyester elastomers that are commercially available include ARNITEL EM460 (manufactured by DMS).

Polyamide Elastomer

The polyamide elastomer may be, for example, a multiblock copolymer in which the hard segment is polyamide and the soft segment is polyether or polyester. Examples of the hard segment include polyamides 6, 66, 610, 11, and 12. Examples of the polyether in the soft segment include polyalkylene glycols such as polyethylene glycol, polypropylene glycol, and polytetramethylene ether glycol. Examples of the polyester in the soft segment include polyethylene adipate and polybutylene-1,4-adipate.

Examples of such polyamide elastomers that are used in the present invention and that are commercially available include PEBAX 5533 (manufactured by Arkema).

The cover layer may further include a compatibilizer. In the present invention, the compatibilizer promotes formation of a homogeneous mixture of the component (a) having the naphthalene structure and the component (b) not having the naphthalene structure. The compatibilizer is preferably a compound having a moiety having an affinity for the component (a) having the naphthalene structure and a moiety having an affinity for the component (b) not having the naphthalene structure (unreactive compatibilizer), or a compound reactive to one or both of the component (a) and the component (b) (reactive compatibilizer), more preferably an unreactive compatibilizer.

Examples of the unreactive compatibilizer include random polymers such as hydrogenated styrene-butadiene rubber, ethylene-propylene rubber, and ethylene-vinyl acetate copolymers, block polymers such as hydrogenated styrene-butadiene copolymers and hydrogenated styrene-based thermoplastic elastomers, and graft polymers in which, to the backbone of polyethylene or polypropylene, polystyrene is grafted.

Examples of the reactive compatibilizer include maleic anhydride-modified polypropylene and ethylene-glycidyl methacrylate copolymers.

Examples of such unreactive compatibilizers that are commercially available include DYNARON (manufactured by JSR Corporation). Examples of such reactive compatibilizers that are commercially available include BOND-FAST (manufactured by Sumitomo Chemical Company, Limited).

The cover layer preferably includes, relative to 100 parts by mass of the total amount of the component (a) and the component (b), 1 part by mass or more and less than 5 parts by mass of the compatibilizer. When the amount of the compatibilizer added satisfies such a range, formation of the phase-separation structure of the cover layer is sufficiently maintained, and adhesiveness between the continuous phase and the separation phase is improved, to provide even higher barrier performance.

Method for Producing Endoscopic Flexible Tube

The component (a) and the component (b) are homogeneously blended together to form a phase-separation state; the resultant covering material is used to cover a flexible-tube base, to thereby obtain an endoscopic flexible tube. The method of covering a flexible-tube base is preferably extrusion covering. Before covering with the covering material is performed, in order to improve adhesiveness between the flexible-tube base 14 and the cover layer 15, an adhesive layer or a primer layer can be formed on the surface of the flexible-tube base 14. The adhesive layer is, for example, a layer formed of a composition constituted by a polymer such as polyurethane and a polyisocyanate compound. The primer layer may be formed of a silane coupling agent, for example.

Endoscopic Medical Apparatus

An endoscopic flexible tube according to the present invention is not limited to endoscopic applications and is widely applicable to endoscopic medical apparatuses. For example, it is also applicable to an endoscope having a distal end equipped with a clip or a wire or an instrument equipped with a basket or a brush, to provide the considerable advantages. Note that the endoscopic medical apparatus is defined to broadly include, in addition to medical apparatuses having the above-described endoscopes as basic structures, medical or medical treatment apparatuses that have flexibility and are introduced into and used within the body, such as remote medical apparatuses.

EXAMPLES

Hereinafter, the present invention will be described further in detail with reference to Examples; however, the present invention is not construed so as to be limited to these.

Examples 1 to 38 and Comparative Examples 1 to 4

Production of Endoscopic-Flexible-Tube-Base-Covering Materials

The raw materials were mixed together so as to satisfy compositions (parts by mass) in Tables 1 to 5, and subjected to, using a twin-screw kneader (product name: KZW15-30MG, manufactured by TECHNOVEL CORPORATION), a melt-kneading treatment at a barrel setting temperature of 270° C. at a number of rotations of the screw of 100 rpm. The ejected resin strands being melted were cooled in a water tank and subsequently turned, using a pelletizer into pellet-shaped endoscopic-flexible-tube-base-covering materials. In each of the covering materials, the polyester resin or polyester elastomer having a naphthalene structure and serving as the component (a) constituted a substantial continuous phase, the thermoplastic resin or thermoplastic elastomer not having a naphthalene structure and serving as the component (b) had a particulate form having a particle size of about 1 μm to about 20 μm to constitute a disperse phase, and the components were in a state of phase separation from each other. Thus, each of the covering materials was, as a whole, in a state of a homogeneous composition, but a phase-separation state was formed.

Production of Resin Sheets

The endoscopic-flexible-tube-base-covering materials obtained above were, using MINI TEST PRESS (manufactured by Toyo Seiki Seisaku-sho, Ltd.), heated at 270° C. and pressed at 10 MPa for 30 seconds, to form thin-film sheets having a thickness of 0.01 mm, a length of 10 cm, and a width of 10 cm (hereafter, also referred to as "polyester sheets").

Test Example 1: Barrier Performance Test

The obtained sheets were subjected to, in accordance with JISZ0208, a water vapor permeability test under temperature-humidity conditions of 60° C. and 90% RH for 96 hours. The determined water vapor permeability was graded into the following barrier-performance evaluation grades to evaluate the water-vapor barrier performance. The results will be described in Tables 1 to 5 below.

Evaluation Grades of Barrier Performance

S: the water vapor permeability is less than 5 $g/m^2 \cdot 96$ hours.

A: the water vapor permeability is 5 $g/m^2 \cdot 96$ hours or more and less than 10 $g/m^2 \cdot 96$ hours.

B: the water vapor permeability is 10 $g/m^2 \cdot 96$ hours or more and less than 20 $g/m^2 \cdot 96$ hours.

C: the water vapor permeability is 20 $g/m^2 \cdot 96$ hours or more and less than 30 $g/m^2 \cdot 96$ hours.

D: the water vapor permeability is 30 $g/m^2 \cdot 96$ hours or more.

Test Example 2: Evaluation of Ozonated-Water Resistance

A polyester sheet produced above was placed into a glass case having a length of 20 cm, a width of 20 cm, and a thickness of 1 cm. The glass case into which the polyester sheet was placed was placed in the channel of an ozonated water generator (trade name, "OWM-10L10P" manufactured by EcoDesign, Inc.) and treated by flowing ozonated water having an ozone concentration of 3 ppm at a flow rate of 1 L/min for 3 hours. Subsequently, the polyester sheet was washed with distilled water, dried at 23° C.×50% RH (relative humidity) for 24 hours, and subsequently subjected to a tensile test using a TENSILON Universal Material Testing Instrument (trade name: RTF-1210, manufactured by A&D Company, Limited). The results were evaluated into the following evaluation grades (a percentage elongation of 100% means elongation by two times). The results will be described in Tables 1 to 5 below.

Evaluation Grades of Ozonated-Water Resistance

S: breakage did not occur even when the percentage elongation reached 200%

A: breakage did not occur even when the percentage elongation reached 150%, but breakage occurred before the percentage elongation reached 200%

B: breakage did not occur even when the percentage elongation reached 100%, but breakage occurred before the percentage elongation reached 150%

C: breakage occurred before the percentage elongation reached 100%

TABLE 1

| | | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|
| Constituent component | 1-1 | 70 | 88 | 52 | — | — | — | 70 | — | — | — | 70 |
| | 1-2 | — | — | — | 70 | 80 | 60 | — | 70 | 85 | 55 | — |
| | 2-1 | 30 | 12 | 48 | — | — | — | — | — | — | — | — |
| | 2-2 | — | — | — | 30 | 20 | 40 | — | — | — | — | — |
| | 2-3 | — | — | — | — | — | — | 30 | — | — | — | — |
| | 2-4 | — | — | — | — | — | — | — | 30 | 15 | 45 | — |
| | 2-5 | — | — | — | — | — | — | — | — | — | — | 30 |
| | 2-6 | — | — | — | — | — | — | — | — | — | — | — |
| | 2-7 | — | — | — | — | — | — | — | — | — | — | — |
| | 2-8 | — | — | — | — | — | — | — | — | — | — | — |
| | 2-9 | — | — | — | — | — | — | — | — | — | — | — |
| | 2-10 | — | — | — | — | — | — | — | — | — | — | — |
| | 2-11 | — | — | — | — | — | — | — | — | — | — | — |
| | 2-12 | — | — | — | — | — | — | — | — | — | — | — |
| | 2-13 | — | — | — | — | — | — | — | — | — | — | — |
| | 2-14 | — | — | — | — | — | — | — | — | — | — | — |
| | 2-15 | — | — | — | — | — | — | — | — | — | — | — |
| | 2-16 | — | — | — | — | — | — | — | — | — | — | — |
| Barrier performance | | S | A | A | S | A | A | B | S | S | S | B |
| Ozonated-water resistance | | S | A | A | A | B | B | B | S | A | A | B |

TABLE 2

| | | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|
| Constituent component | 1-1 | — | 70 | — | 70 | — | 70 | — | 70 | — | 70 | — |
| | 1-2 | 70 | — | 70 | — | 70 | — | 70 | — | 70 | — | 70 |
| | 2-1 | — | — | — | — | — | — | — | — | — | — | — |
| | 2-2 | — | — | — | — | — | — | — | — | — | — | — |
| | 2-3 | — | — | — | — | — | — | — | — | — | — | — |
| | 2-4 | — | — | — | — | — | — | — | — | — | — | — |
| | 2-5 | — | — | — | — | — | — | — | — | — | — | — |
| | 2-6 | 30 | — | — | — | — | — | — | — | — | — | — |
| | 2-7 | — | 30 | — | — | — | — | — | — | — | — | — |

TABLE 2-continued

|  | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|
| 2-8 | — | — | 30 | — | — | — | — | — | — | — | — |
| 2-9 | — | — | — | 30 | — | — | — | — | — | — | — |
| 2-10 | — | — | — | — | 30 | — | — | — | — | — | — |
| 2-11 | — | — | — | — | — | 30 | — | — | — | — | — |
| 2-12 | — | — | — | — | — | — | 30 | — | — | — | — |
| 2-13 | — | — | — | — | — | — | — | 30 | — | — | — |
| 2-14 | — | — | — | — | — | — | — | — | 30 | — | — |
| 2-15 | — | — | — | — | — | — | — | — | — | 30 | — |
| 2-16 | — | — | — | — | — | — | — | — | — | — | 30 |
| Barrier performance | B | B | A | B | B | B | B | B | B | B | B |
| Ozonated-water resistance | B | B | B | B | B | B | B | B | B | B | A |

TABLE 3

|  |  | Example 23 | Example 24 | Example 25 | Example 26 | Example 27 | Example 28 | Example 29 | Example 30 |
|---|---|---|---|---|---|---|---|---|---|
| Constituent component | 1-1 | 75 | 88 | 53 | — | — | — | 65 | — |
|  | 1-2 | — | — | — | 75 | 85 | 55 | — | 65 |
|  | 2-4 | — | — | — | — | — | — | — | — |
|  | 3-1 | 25 | 12 | 47 | — | — | — | — | — |
|  | 3-2 | — | — | — | 25 | 15 | 45 | — | — |
|  | 3-3 | — | — | — | — | — | — | 35 | — |
|  | 3-4 | — | — | — | — | — | — | — | 35 |
|  | 3-5 | — | — | — | — | — | — | — | — |
|  | 3-6 | — | — | — | — | — | — | — | — |
|  | 4-1 | — | — | — | — | — | — | — | — |
|  | 4-2 | — | — | — | — | — | — | — | — |
|  | 5-1 | — | — | — | — | — | — | — | — |
| Barrier performance |  | S | A | A | S | S | A | B | B |
| Ozonated-water resistance |  | S | A | A | S | A | A | B | B |

TABLE 4

|  |  | Example 31 | Example 32 | Example 33 | Example 34 | Example 35 | Example 36 | Example 37 | Example 38 |
|---|---|---|---|---|---|---|---|---|---|
| Constituent component | 1-1 | 70 | — | 85 | — | 53 | — | 85 | 53 |
|  | 1-2 | — | 70 | — | 85 | — | 53 | — | — |
|  | 2-4 | — | — | 15 | 15 | — | — | 15 | — |
|  | 3-1 | — | — | — | — | — | — | — | — |
|  | 3-2 | — | — | — | — | — | — | — | — |
|  | 3-3 | — | — | — | — | — | — | — | — |
|  | 3-4 | — | — | — | — | 47 | 47 | — | 47 |
|  | 3-5 | 30 | — | — | — | — | — | — | — |
|  | 3-6 | — | 30 | — | — | — | — | — | — |
|  | 4-1 | — | — | 4 | — | 1 | — | 10 | 0.5 |
|  | 4-2 | — | — | — | 4 | — | 1 | — | — |
|  | 5-1 | — | — | — | — | — | — | — | — |
| Barrier performance |  | B | B | S | S | S | S | B | B |
| Ozonated-water resistance |  | B | B | S | S | A | A | S | A |

TABLE 5 / TABLE 5-continued

|  |  | Comparative Example 1 | Comparative Example 2 | Comparative Example 3 | Comparative Example 4 |
|---|---|---|---|---|---|
| Constituent component | 1-1 | 100 | 45 | 40 | 100 |
|  | 1-2 | — | — | — | — |
|  | 2-4 | — | 55 | — | — |
|  | 3-1 | — | — | 60 | — |
|  | 3-2 | — | — | — | — |
|  | 3-3 | — | — | — | — |
|  | 3-4 | — | — | — | — |
|  | 3-5 | — | — | — | — |
|  | 3-6 | — | — | — | — |
|  | 4-1 | — | — | — | — |
|  | 4-2 | — | — | — | — |
|  | 5-1 | — | — | — | 0.2 |

60

65

TABLE 5-continued

|  | Comparative Example 1 | Comparative Example 2 | Comparative Example 3 | Comparative Example 4 |
|---|---|---|---|---|
| Barrier performance | C | D | D | C |
| Ozonated-water resistance | B | C | C | C |

Descriptions of Terms in Tables

Compounds Used in EXAMPLES 1-1: polyester elastomer having naphthalene structure (trade name: PELPRENE EN, manufactured by TOYOBO CO., LTD.)

1-2: polyester resin having naphthalene structure (trade name: TQB-OT, manufactured by Teijin Chemicals Ltd., polybutylene naphthalate)

2-1: polyolefin resin (trade name: NOVATEC PP, manufactured by Japan Polypropylene Corporation)

2-2: polydiene resin (trade name: JSR1500, manufactured by JSR Corporation)

2-3: polyacrylic resin (trade name: ACRYPET VH, manufactured by Mitsubishi Chemical Corporation)

2-4: polystyrene resin (trade name: CEVIAN N, manufactured by Daicel Corporation)

2-5: polyvinyl resin (trade name: KANEVINYL M1008, manufactured by KANEKA CORPORATION)

2-6: polyester resin (trade name: NOVADURAN 5010CR2, manufactured by Mitsubishi Chemical Corporation)

2-7: polyamide resin (trade name: UBESTA, manufactured by Ube Industries, Ltd.)

2-8: polycarbonate resin (trade name: IUPILON S-2000, manufactured by Mitsubishi Chemical Corporation)

2-9: polyurethane resin (trade name: VULKOLLAN, manufactured by Bayer AG)

2-10: polyether resin (trade name: VICTREX PEEK, manufactured by Victrex plc.)

2-11: polyether resin (trade name: IUPIACE, manufactured by Mitsubishi Engineering-Plastics Corporation, polyphenylene ether)

2-12: polysulfone resin (trade name: UDEL P1700, manufactured by Solvay)

2-13: polysulfone resin (trade name: RADEL A, manufactured by Solvay, polyethersulfone)

2-14: polyether resin (trade name: polyether imide, manufactured by SABIC, polyether imide)

2-15: polyamide resin (trade name: TI-5013, manufactured by Toray Industries, Inc., polyamide-imide)

2-16: fluorine-containing resin (trade name: NEOFLON PFA, manufactured by DAIKIN INDUSTRIES, LTD.)

3-1: polystyrene elastomer (trade name: TEFABLOC 4300C, manufactured by Mitsubishi Chemical Corporation)

3-2: polyolefin elastomer (trade name: EXCELINK 1700B, manufactured by JSR Corporation)

3-3: polyvinyl chloride elastomer (trade name: SUNPRENE F1469, manufactured by Mitsubishi Chemical Corporation)

3-4: polyurethane elastomer (trade name: MIRACTRAN E385, manufactured by Nippon Miractran Company Limited)

3-5: polyester elastomer (trade name: ARNITEL EM460, manufactured by DMS)

3-6: polyamide elastomer (trade name: PEBAX 5533, manufactured by Arkema)

4-1: unreactive compatibilizer (trade name: DYNARON, manufactured by JSR Corporation)

4-2: reactive compatibilizer (trade name: BONDFAST, manufactured by Sumitomo Chemical Company, Limited)

5-1: cross-linking agent (trade name: CARBODILITE LA-1, manufactured by Nisshinbo Industries, Inc.)

2-1 to 5-1 above do not have naphthalene structures.

As is clear from Table 1 to Table 5, when the covering material was constituted by a single resin having a naphthalene structure without formation of a phase-separation structure, the resultant sheet had poor water-vapor barrier performance (Comparative Example 1); addition of a compatibilizer also resulted in poor ozonated-water resistance (Comparative Example 4). Even in the case where the covering material was a blend of the component (a) and the component (b) and a phase-separation structure was formed, the component (a) content lower than that defined in the present invention resulted in both of poor barrier performance and poor ozonated-water resistance (Comparative Examples 2 and 3).

By contrast, when the covering material was a blend of the component (a) and the component (b), a phase-separation structure was formed, and the contents satisfied features according to the present invention 1, this covering material provided a thin-film sheet having a thickness of 0.01 mm having high water-vapor barrier performance and high ozonated-water resistance (Examples 1 to 38). In addition, it has been demonstrated that, when the covering material is a blend of the component (a) and the component (b), addition of a compatibilizer is effective for improving both of the barrier performance and the ozonated-water resistance of the resultant sheet.

The present invention has been described together with embodiments thereof; however, we do not intend to limit our invention in any minor portion of the descriptions unless otherwise specified; we believe that the invention is construed broadly without departing from the spirit and scope of the invention described in the attached claims.

REFERENCE SIGNS LIST 2 electronic endoscope (endoscope)
3 insertion section
3a flexible tube
3b angle portion
3c distal-end portion
5 main-body operation section
6 universal cord
11 spiral tube
11a metal strip
12 sleeve-shaped mesh body
13 metal cap
14 flexible-tube base
15 cover layer

What is claimed is:

1. An endoscopic flexible tube comprising a sleeve-shaped flexible-tube base having flexibility, and a cover layer for the flexible-tube base, wherein the cover layer contains components (a) and (b) below and, in the cover layer, a ratio of the component (a) to a total amount of the components (a) and (b) is 53 mass % or more and less than 90 mass %:

wherein the component (a) is (a2) a polyester elastomer having a naphthalene structure; and the component (b) is (b2) a thermoplastic elastomer not having a naphthalene structure, and wherein, in the cover layer, the component (a) and the component (b) are phase-separated from each other.

2. The endoscopic flexible tube according to claim 1, wherein the (b2) thermoplastic elastomer not having a naphthalene structure includes at least one of a polystyrene elastomer, a polyolefin elastomer, a polyvinyl chloride elastomer, a polyurethane elastomer, a polyester elastomer, or a polyamide elastomer.

3. The endoscopic flexible tube according to claim 2, wherein the (b2) thermoplastic elastomer not having a naphthalene structure includes at least one of a polystyrene elastomer or a polyolefin elastomer.

4. The endoscopic flexible tube according to claim 1, wherein the cover layer contains a compatibilizer.

5. An endoscopic medical apparatus comprising the endoscopic flexible tube according to claim 1.

6. An endoscopic-flexible-tube-base-covering material comprising components (a) and (b) below, wherein a ratio of the component (a) to a total amount of the components (a) and (b) is 53 mass % or more and less than 90 mass %:

wherein the component (a) is (a2) a polyester elastomer having a naphthalene structure; and the component (b) is (b2) a thermoplastic elastomer not having a naphthalene structure, and wherein, in the cover layer, the component (a) and the component (b) are phase-separated from each other.

* * * * *